United States Patent
Amend et al.

(10) Patent No.: US 7,046,347 B1
(45) Date of Patent: May 16, 2006

(54) INSTRUMENT WITH COLORIMETER AND SENSOR INPUTS FOR INTERFACING WITH A COMPUTER

(76) Inventors: John R. Amend, 2135 Baxter Dr., Bozeman, MT (US) 59715; Dale A. Hammond, 55-705 Wahineppee St., Laie, HI (US) 96762

(*) Notice: Subject to any disclaimer, the term of this patent is extended or adjusted under 35 U.S.C. 154(b) by 447 days.

(21) Appl. No.: 10/113,821

(22) Filed: Mar. 29, 2002

Related U.S. Application Data
(60) Provisional application No. 60/280,674, filed on Mar. 30, 2001.

(51) Int. Cl.
*G01J 3/50* (2006.01)
*G01N 21/49* (2006.01)

(52) U.S. Cl. .................... 356/73; 356/338; 356/402
(58) Field of Classification Search ........... 356/343, 356/337, 338, 73, 402, 441, 442; 250/573, 250/574
See application file for complete search history.

(56) References Cited

U.S. PATENT DOCUMENTS 3,553,462 A * 1/1971 Johnson .................. 356/343
5,140,168 A * 8/1992 King ...................... 356/442
5,313,267 A * 5/1994 MacFarlane et al. ....... 356/405

* cited by examiner

*Primary Examiner*—F. L. Evans
(74) *Attorney, Agent, or Firm*—Richard C. Conover

(57) ABSTRACT

An array of multiple light-emitting diodes each having a different wavelength are equally spaced around a tubular sample holder facing inwardly. A photo-diode light sensor that detects light transmitted through the sample is mounted to the tubular sample holder at a position directly opposite each light-emitting diode. By selectively turning on one of the LED's and selecting the associated photo-diode exactly opposite it, the light transmission through a solution can be ascertained. A computer is then used to plot the transmission and absorption on a graph for each of the different wavelengths. The circular array of sensors and LED's results in one sensor directly opposite each LED, one sensor off-axis on either side in the forward scatter direction, and one sensor off-axis on either side in the back scatter direction. The combination of back-scattered light and forward-scattered light and transmitted light permits measurements of the turbidity of the sample solution.

6 Claims, 8 Drawing Sheets

INSTRUMENT WITH COLORIMETER AND SENSOR INPUTS FOR INTERFACING WITH A COMPUTER

SPECIFICATION

This application claims the benefit of Provisional Application Ser. No. 60/280,674, filed Mar. 30, 2001.

BACKGROUND OF INVENTION

This invention relates to a diode array colorimeter instrument for measuring light transmission through a test sample and for measuring the turbidity of the test sample.

Colorimetry and spectrophotometry, analytical techniques based on passing light through a colored solution, are the most widely chemical used analysis method in medicine, chemistry, water quality, and environmental science. Spectrophotometry involves relatively high cost instruments that use a continuously variable wavelength of light of quite narrow bandwidth, while colorimetry involves lower cost instruments with several selectable wavelengths or colors and wider bandwidth. Colored solutions absorb certain wavelengths of light because of electron energy level spacings within the absorbing molecule. Absorption of a specific wavelength of light is related to the concentration of the absorbing molecule. Colorimetric measurements, while generally lacking in flexibility because of wavelength limitations, are often of completely adequate quality for environmental and educational use.

Visible-spectrum spectrophotometers use a white light source and either a prism or diffraction grating to select the wavelength of light to pass through the sample. The prism or diffraction grating requires a relatively expensive calibrated moving mechanical mount, and the small amount of light that reaches the sample often requires sensitive photo detectors, thus placing a relatively high baseline cost on these instruments.

Colorimeters use either a white light source and an optical filter to select wavelength or, in the alternative, use light-emitting-diodes to produce light beams having wavelengths. These are switch selected, and the instrument is operated at only one wavelength.

A diode array spectrophotometer uses white light to illuminate the sample, a prism or diffraction grating to separate the white light into a spectrum after passing through the sample, and then an array of 100 or 256 extremely small photo-diodes, each viewing a different color of wavelength of light. The signals from this diode array are scanned electronically and transmitted to a computer for display and analysis. An example of such a spectrophotometer is shown in U.S. Pat. No. 5,477,326 to Dosmann. The diode array spectrophotometer is the most flexible and most expensive of the spectrophotometric instrument family.

While concentration is measured by determining the absorption of a colored light beam passing through a sample, turbidity is measured by observing light scattered to the side as the light beam passes through the sample. Turbidity is of value in determining the concentration of extremely small colloidal particles suspended in a solution. Historically different instruments have been used for measurement of transmitted and scattered light.

SUMMARY OF INVENTION

An array of multiple light-emitting diodes each having a different wavelength are equally spaced around a tubular sample holder facing inwardly. A photo-diode light sensor that detects light transmitted through the sample is mounted to the tubular sample holder at a position directly opposite each light-emitting diode. By selectively turning on one of the LED's and selecting the associated photo-diode exactly opposite it, the light transmission through a solution can be ascertained. A computer is then used to plot the transmission and absorption on a graph for each of the different wavelengths. The circular array of sensors and LED's results in one sensor directly opposite each LED, one sensor off-axis on either side in the forward scatter direction, and one sensor off-axis on either side in the back scatter direction. The combination of back-scattered light and forward-scattered light and transmitted light permits measurements of the turbidity of the sample solution.

DESCRIPTION OF THE DRAWINGS

In order that the invention may be clearly understood and readily carried into effect, a preferred embodiment of the invention will now be described, by way of example only, with reference to the accompanying drawings wherein.

DESCRIPTION OF A PREFERRED EMBODIMENT

Figure 1:
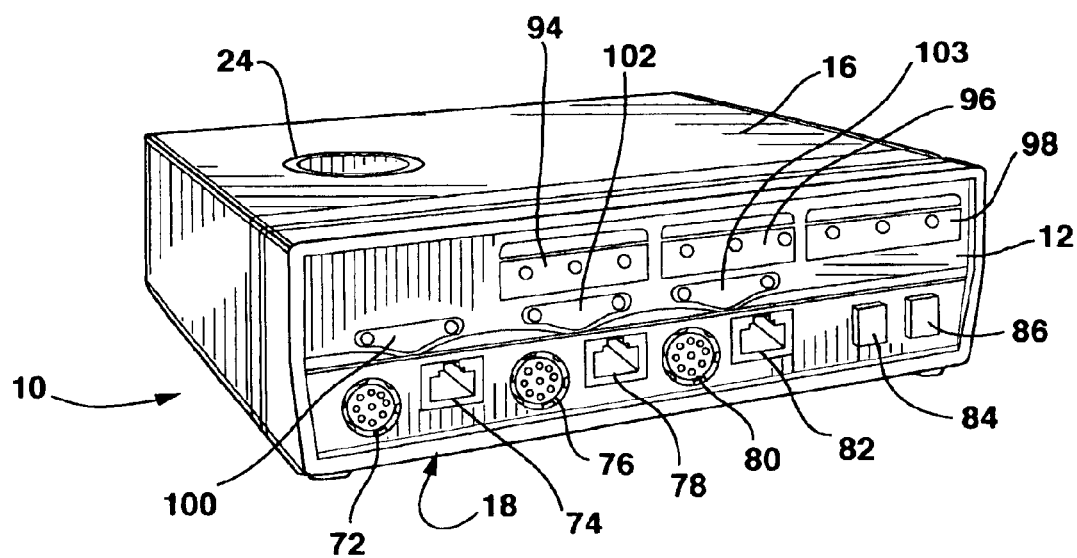
FIG. 1 is a perspective view of a diode array colorimeter instrument according to the present invention.
Figure 2:
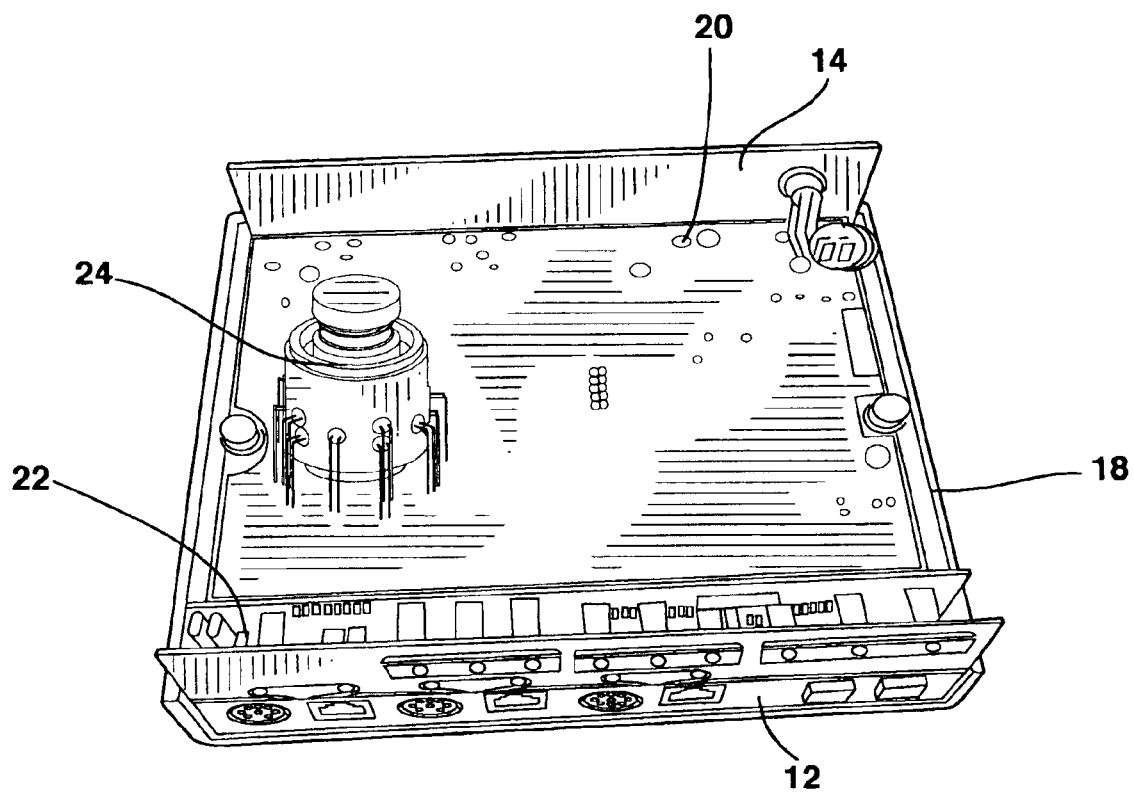
FIG. 2 is a perspective front view of the instrument shown in FIG. 1 with the top cover removed.
Figure 3:
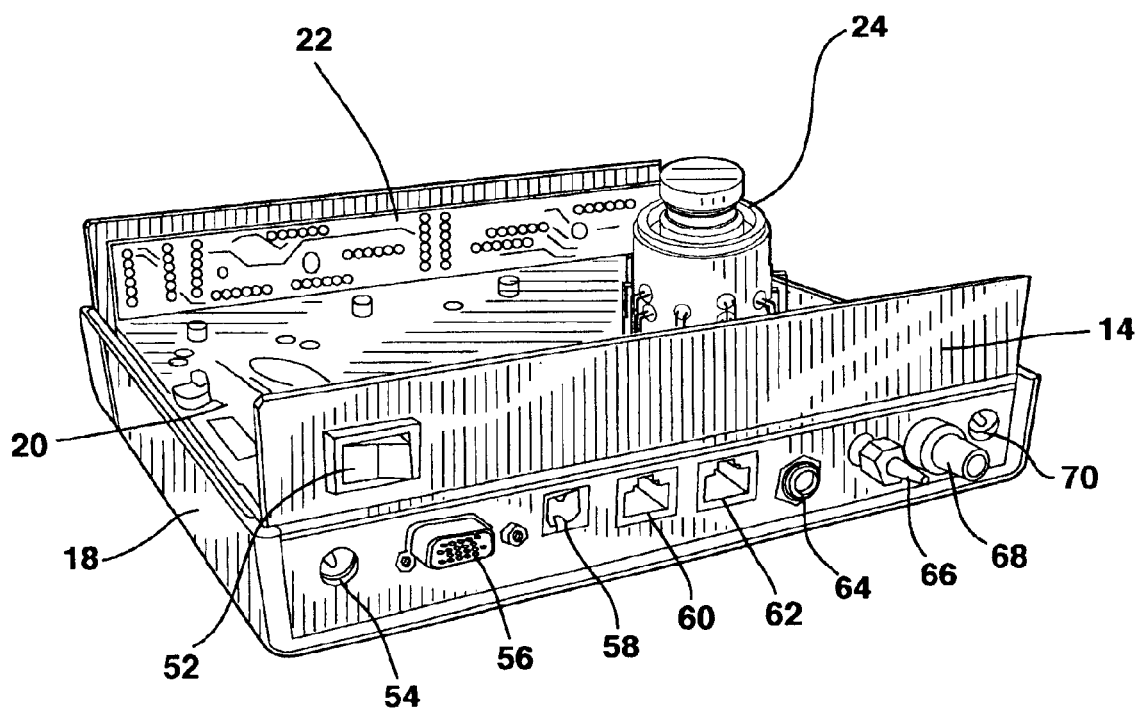
FIG. 3 is a perspective rear view of the instrument shown in FIG. 1 with the cover removed.

A diode array colorimeter instrument 10 according to the present invention is shown in FIGS. 1–7. Instrument 10 includes a front panel 12, a rear panel 14, a top cover 16 extending partially down the sides of instrument 10 as shown in FIG. 1, and a bottom cover 18 extending partially up the sides to meet and abut the top cover 16 as shown in FIGS. 2 and 3. A main circuit board 20 is installed within the instrument 10, as shown in FIGS. 2 and 3, and a circuit board 22 for controlling the front panel display is installed within instrument 10, as shown in FIGS. 2 and 3.

Figure 4:
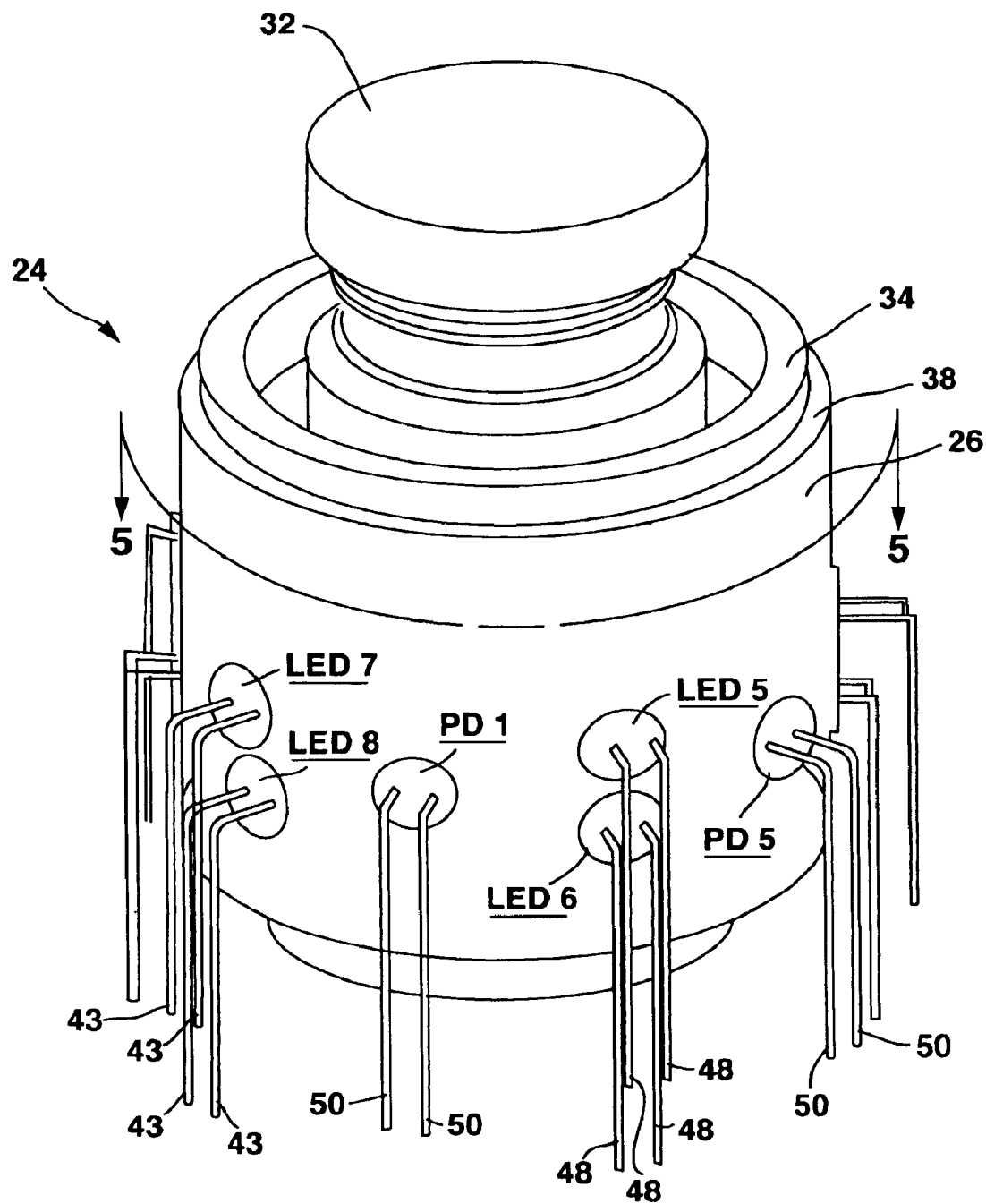
FIG. 4 is an enlarged view of a diode array test sample holder mounted in the instrument as shown in FIG. 2.
Figure 6:
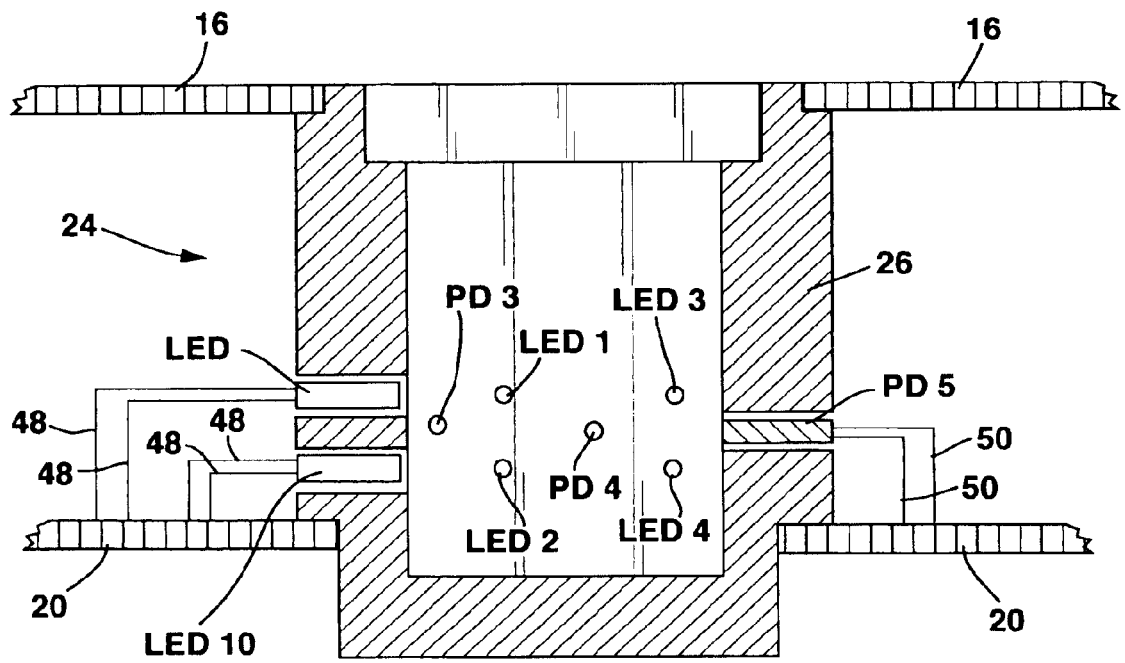
FIG. 6 is a cross-sectional view of the test sample holder taken along line 6—6 in FIG. 5.

A diode array test sample holder 24 is mounted to circuit board 20 as shown in FIGS. 2 and 3. Test sample holder 24 in includes a tubular body 26, as shown in FIG. 4, extending around a longitudinal axis 28, as shown in FIG. 6, with a hollow interior 30. The hollow interior 30 is sized to accept a transparent cylindrical vial 32, as shown in FIG. 4.

The body 26 of sample holder 24 includes an upper annular ridge 34 which is sized to fit within a corresponding opening 36 provided in top cover 16, as shown in FIGS. 1 and 6. The top cover 16 rests on a ledge 38, as shown in FIG. 6. A further annular bore 40 is provided at the top end of colorimeter body 26, as shown in FIG. 6, which provides a ledge 42 which supports a light shield (not shown) for covering the interior 30 of colorimeter body 26 when vial 32 is positioned within hollow interior 30.

An annular portion of the lower end of body 26 is removed leaving a stem 42, as shown in FIG. 6. The stem 42 is sized to have a diameter to be slidably received by a correspondingly sized bore 44 in circuit board 20, as shown in FIG. 6. The portion of body 26 above stem portion 42 rests on circuit board 20.

Figure 5:
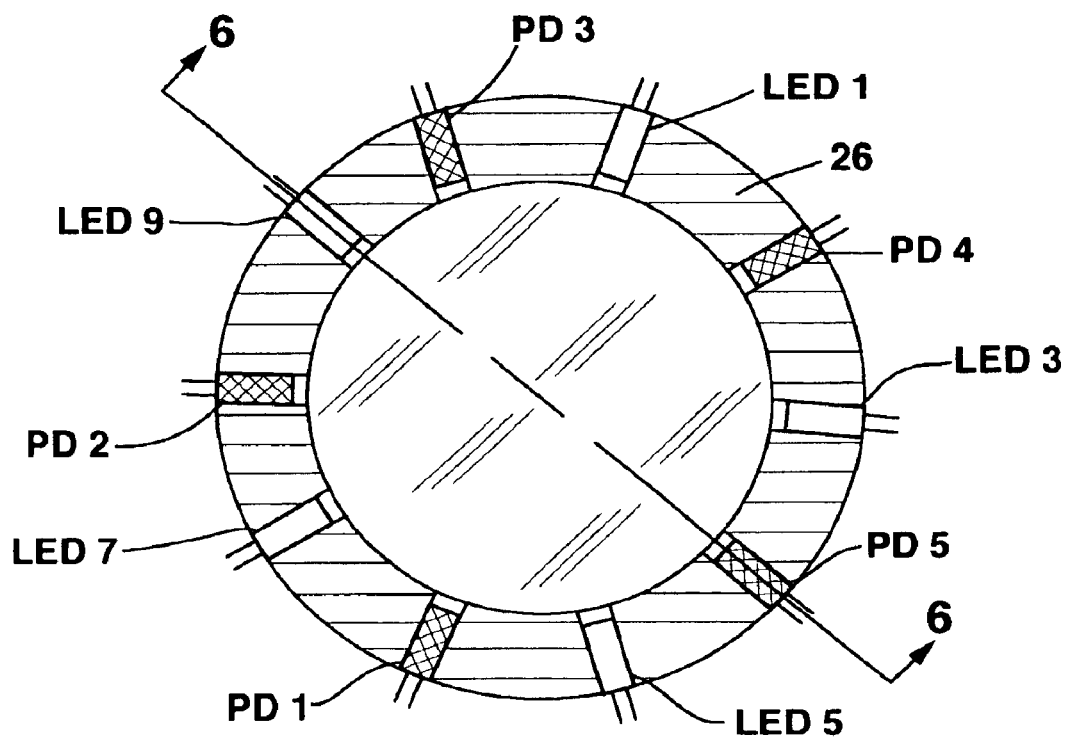
FIG. 5 is a schematic cross-sectional view of the test sample holder taken generally along the line 5—5 in FIG. 4.

In a preferred embodiment, the diode array test sample holder 24 includes five pairs of light-emitting diodes LED 1 and 2, LED 3 and 4, LED 5 and 6, LED 7 and 8 and LED 9 and 10, which pairs are equally spaced around the circumference of body 26 in 36° increments, as shown in FIG. 5. Each light-emitting diode of a pair is mounted one above the other, as shown in FIG. 6. Five photo-diode light sensors PD1, PD2, PD3, PD4 and PD5 are equally spaced around the periphery of body 26, as shown in FIG. 5, with each photo-diode light sensor positioned diametrically opposite a pair of light-emitting diodes, as shown in FIGS. 5 and 6. The photo-diode light sensors are positioned so that distance between one LED of each pair to the centerline of an associated light sensor is the same as the distance between the second LED of each pair to the centerline of this light sensor. For example, PD5 is located opposite LED 9 and 10, as shown in FIG. 6. In this example, the light emitted by either LED 9 or LED 10 is detected by PD5. Light-emitting diodes LED 1–LED 10 and photo-diode light sensors PD1–PD5 are glued into place in associated holes 46 provided in body 26.

Each light-emitting diode LED 1–LED 10 is operated at a different frequency (wave length) thus providing ten sampling frequencies crossing diode array test sample holder 24 and shining through vial 26.

Electrical circuitry on main circuit board 20 is used to control the switching between various light-emitting diodes and associated photo-diodes and to read out the light transmission received by a particular photo-diode. A pair of leads 48 are connected to each LED, as shown in FIG. 4, and a pair of leads 50 are connected to each photo-diode light sensor, again as shown in FIG. 4. These leads are connected into the appropriate circuitry on circuit board 20.

Figure 7:
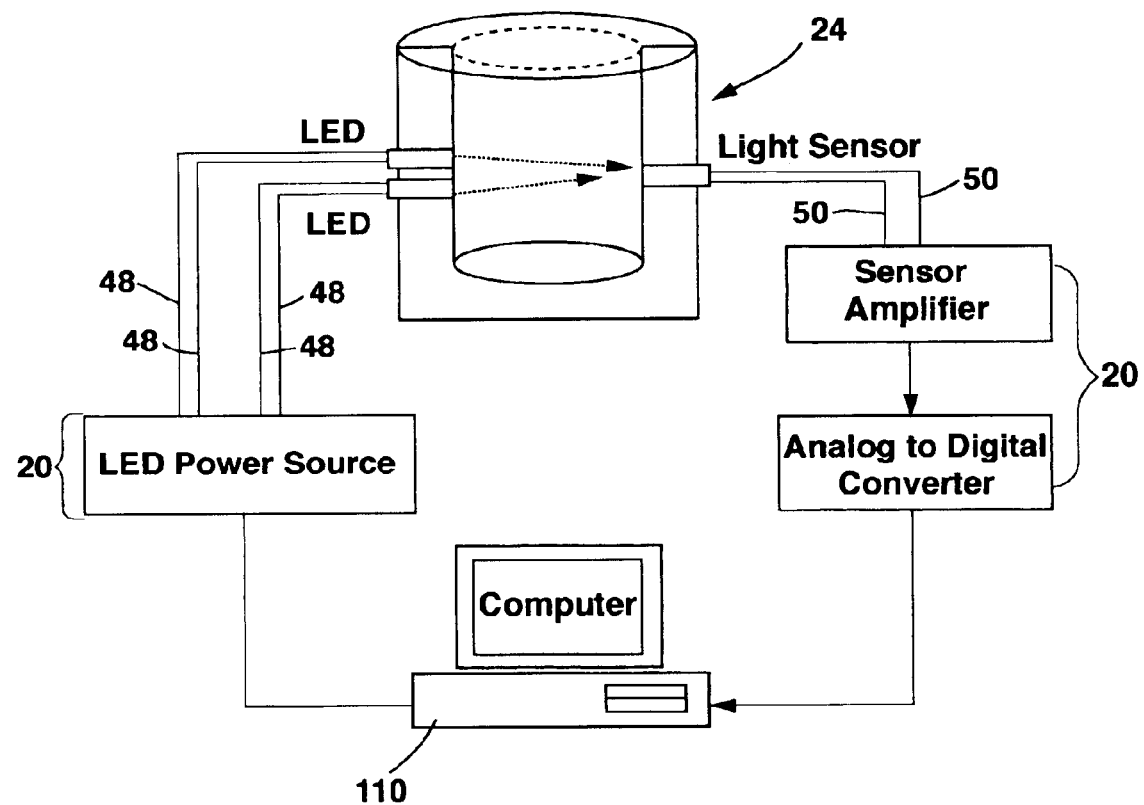
FIG. 7 is a schematic diagram of the complete colorimeter system.
Figure 8:
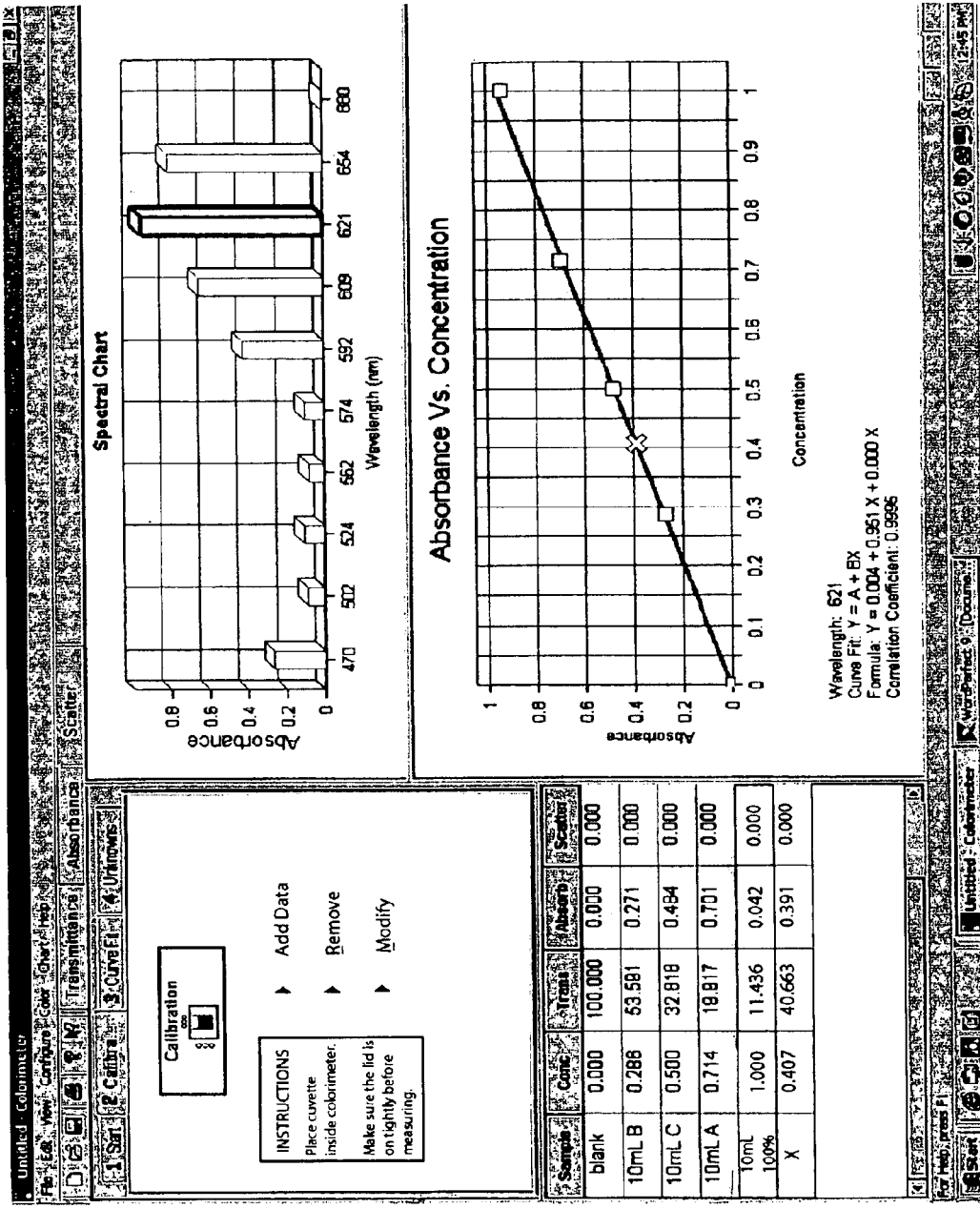
FIG. 8 is a computer generated presentation showing results of a colorimeter analysis of a solution.

The analog output signals of the photo detectors are converted to digital output signals by the circuit board 20. These digital output signals are then directed to a computer 110, as shown in FIG. 7, which computer includes software for reading the output of each photo-diode light sensor, and for determining and printing out, histograms of the transmissions received from each of the ten light-emitting diodes. FIG. 8 is a printout of the data produced from a diode array colorimeter using a diode array having ten LEDs and associated photo-diode detectors. Although a preferred embodiment, as described herein, includes ten LED diode arrays, the invention could be used with six or fourteen diode arrays, or any number of other arrays, all of which are included within the scope of the present invention.

In addition, the electrical circuitry incorporated in circuit board 20 can also read and analyze backscatter information received from the photo-diode light sensors on either side of an operating light-emitting diode. The computer software uses this information to determine turbidity (scattered light) from the sample. Turbidity is of value for scientists in determining the concentration of extremely small colloidal particles.

The electrical circuitry in circuit board 20 includes an analog to digital converter which includes circuitry for providing an extremely fast response time. There is additional circuitry which provides a slower response time, but more resolution.

The rear panel 14 of the instrument 10 is shown in FIG. 3. Rear panel 14 includes a number of switches and jacks. On/Off switch 52; a 12Vac jack 54; R-232 cable connector 56; Universal Serial Bus 58; Smart Sensor Ports 60 and 62; Counter jack 64; Pressure jack 66; PH port 68 and Ground jack 70 are identified on the rear panel of FIG. 3.

The front panel 12 of the instrument 10 is shown in FIG. 1. As shown in FIG. 1, a Universal Sensor Port A includes a round sensor port 72 and a rectangular sensor port 74; Universal Sensor Port B includes a round sensor port 76 and a rectangular sensor port 78 and Universal Sensor Port C includes a round sensor port 80 and a rectangular sensor port 82. The Universal Sensor Ports will accept the output of MICROLAB, VERNIER and PASCO sensors.

Auto scaling input amplifiers, included in the electrical circuitry, permit the Universal Sensor Ports to accept a signal from any sensor that produces a voltage in the +/− 10 volt range or a current in the +/− 2.5 milliampere range, or a digital signal in the +/− 2.5 volt range.

A mark switch 84, shown in FIG. 1, permits a researcher to exactly mark or flag a visually observed occurrence in an experiment. This switch directly accesses a microprocessor to interrupt line, which flags the data and logs the time within microseconds of the switch command. A Start/Stop switch 86, shown in FIG. 1, is used to start and stop an experiment, and will respond within microseconds to a command.

The front panel circuit board 22 controls the display lights of the front panel 12. Timer lights 94, colorimeter lights 96 and sensor lights 98 Sensor Port A lights 100, Sensor Port B lights 102 and Sensor Port C lights 104 and a Smart Port indicator light 106 is shown in FIG. 1.

In operating the diode array colorimeter instrument 10, a "blank" of pure water is placed in vial 32, and the vial placed in the hollow interior 30 of test sample holder 24. The pure water is used to calibrate the system. When the LEDs are turned on, one hundred percent of the light will be transmitted along the path with no absorption and no backscatter. Each light path can then be optimized with the electrical circuitry by increasing the power of each LED in steps to provide a full scale digital readout at the photo-diode associated with each light path. The internal circuitry then "remembers" the current to the LED which provides this maximum. This procedure reduces the noise on each light path. Also, the amount of current associated with producing a full scale capacity at the photo-diode is stored in the integrated circuit and used again each time a particular LED-PD path is used during subsequent experiments.

When it is desired to analyze an unknown sample, vial 32 is filled with the unknown solution, and the vial placed in the hollow interior 30 of test sample holder 24. The ten LEDs are then actuated with software provided in computer 110, causing ten different light frequencies to be transmitted through the unknown solution. The output data is then used to determine transmission, absorption and concentration of light passing through the unknown sample. A computer printout of the resulting analysis, an example of which is shown in FIG. 8, can then be printed out for a complete analysis of the unknown solution.

Further, the circular array of light sensors and LED's results in one sensor directly opposite each LED (180°), one sensor off-axis on either side in the forward scatter direction (134°), and one sensor off-axis on either side of the back scatter direction (72°). The combination of back-scattered light, forward-scattered light and transmitted (absorbed) light permits measurement of the turbidity of the sample solution.

While the fundamental novel features of the invention have been shown and described, it should be understood that various substitutions, modifications and variations may be made by those skilled in the art without departing from the spirit or scope of the invention. Accordingly, all such modifications or variations are included in the scope of the invention as described by the following claims:

We claim:

1. A colorimeter arranged to provide light transmission and scatter measurements through a test sample comprising:
    a tubular body test sample holder having a longitudinal axis of rotation;
    at least a pair of light-emitting diodes mounted to the tubular body one above the other in a direction parallel to the longitudinal axis, the light-emitting diodes facing the longitudinal axis for emitting light toward the longitudinal axis; and
    a plurality of photo-diode light sensors mounted to the tubular body facing the longitudinal axis with each photo-diode positioned directly opposite a corresponding light-emitting diode for detecting light transmitted through the test sample from the corresponding light-emitting diode and for detecting light scattered by the test sample by other light-emitting diodes and providing a signal output depending on the amount of light detected.

2. The colorimeter according to claim 1 wherein each light-emitting diode is operated at a different frequency.

3. The colorimeter according to claim 1 wherein the plurality of light-emitting diodes are equally spaced circumferentially around the tubular body.

4. The colorimeter according to claim 1 further including an electrical circuit board for actuating selected light-emitting diodes and selected photo-diodes.

5. The colorimeter according to claim 1 further including a computer for analyzing the output signals of the photo-diodes to determine transmission, absorption of light passing through a test sample and scatter of light reflected from the test sample.

6. The colorimeter according to claim 1 wherein ten light-emitting diodes are arranged in five pairs equally spaced circumferentially around the tubular body with one light-emitting diode of each pair mounted above the other in a direction parallel to the-longitudinal axis and further wherein each light-emitting diode is operated at a different frequency and further wherein a single photo-diode is positioned directly opposite a corresponding pair of light-emitting diodes whereby light transmission, absorbance and scatter may be measured at ten different frequencies and at least three different angles.

* * * * *